US012397284B2

(12) United States Patent
Limbach et al.

(10) Patent No.: US 12,397,284 B2
(45) Date of Patent: Aug. 26, 2025

(54) PROCESS AND CATALYST FOR OXIDATIVE ESTERIFICATION WITH LONG-LIFE CATALYST

(71) Applicants: Dow Global Technologies LLC, Midland, MI (US); Rohm and Haas Company, Collegeville, PA (US)

(72) Inventors: Kirk W. Limbach, Dresher, PA (US); Christopher D. Frick, Pottstown, PA (US); Wen Sheng Lee, Midland, MI (US); Victor J. Sussman, Midland, MI (US); Dmitry A. Krapchetov, Lansdale, PA (US); Jeffrey A. Herron, Midland, MI (US)

(73) Assignees: DOW GLOBAL TECHNOLOGIES LLC, Midland, MI (US); ROHM AND HAAS COMPANY, Collegeville, PA (US)

( * ) Notice: Subject to any disclaimer, the term of this patent is extended or adjusted under 35 U.S.C. 154(b) by 463 days.

(21) Appl. No.: 17/908,041

(22) PCT Filed: Mar. 15, 2021

(86) PCT No.: PCT/US2021/022283
§ 371 (c)(1),
(2) Date: Aug. 30, 2022

(87) PCT Pub. No.: WO2021/188403
PCT Pub. Date: Sep. 23, 2021

(65) Prior Publication Data
US 2023/0113685 A1    Apr. 13, 2023

Related U.S. Application Data

(60) Provisional application No. 62/990,482, filed on Mar. 17, 2020.

(51) Int. Cl.
| | |
|---|---|
| *B01J 23/52* | (2006.01) |
| *B01J 21/06* | (2006.01) |
| *B01J 35/30* | (2024.01) |
| *B01J 35/45* | (2024.01) |
| *B01J 37/02* | (2006.01) |
| *C07C 67/39* | (2006.01) |

(52) U.S. Cl.
CPC .............. *B01J 23/52* (2013.01); *B01J 21/063* (2013.01); *B01J 35/397* (2024.01); *B01J 37/0201* (2013.01); *C07C 67/39* (2013.01); *B01J 35/393* (2024.01); *B01J 35/45* (2024.01); *B01J 2235/00* (2024.01); *B01J 2235/30* (2024.01)

(58) Field of Classification Search
CPC . B01J 23/52; B01J 35/23; B01J 35/397; B01J 21/063; B01J 37/0201; C07C 67/39
USPC .............. 502/325, 330, 339, 350, 243, 262; 977/773
See application file for complete search history.

(56) References Cited

U.S. PATENT DOCUMENTS

| | | | | |
|---|---|---|---|---|
| 4,537,873 | A * | 8/1985 | Kato | B01J 23/40 502/262 |
| 5,932,750 | A * | 8/1999 | Hayashi | B01J 23/66 549/523 |
| 6,228,800 | B1 | 5/2001 | Yamaguchi et al. | |
| 6,984,607 | B2 * | 1/2006 | Kuperman | B01J 23/66 502/344 |
| 7,326,806 | B2 | 2/2008 | Hayashi et al. | |
| 2010/0008840 | A1 * | 1/2010 | Zhong | B01J 35/23 502/343 |
| 2011/0111952 | A1 * | 5/2011 | Shiratori | F01N 3/2803 977/773 |
| 2011/0184206 | A1 | 7/2011 | Suzuki et al. | |
| 2012/0329643 | A1 * | 12/2012 | Ogawa | H01M 4/926 502/355 |
| 2019/0084914 | A1 | 3/2019 | Krill et al. | |
| 2020/0156047 | A1 * | 5/2020 | Sussman | B01J 35/396 |
| 2024/0400492 | A1 * | 12/2024 | Limbach | C07C 67/39 |
| 2024/0400493 | A1 * | 12/2024 | Limbach | B01J 23/52 |

FOREIGN PATENT DOCUMENTS

| | | | | |
|---|---|---|---|---|
| EP | 1393800 A1 | 3/2004 | | |
| JP | H02290251 A * | 11/1990 | ............. | B01D 53/94 |
| JP | 2004181357 A | 7/2004 | | |
| JP | 2004181359 A | 7/2004 | | |
| WO | 2019139719 A1 | 7/2019 | | |
| WO | 2020005693 A1 | 1/2020 | | |

* cited by examiner

*Primary Examiner* — Patricia L. Hailey
(74) *Attorney, Agent, or Firm* — CANTOR COLBURN LLP

(57) ABSTRACT

A catalyst comprising noble metal particles and titanium-containing particles. The noble metal particles and titanium-containing particles are disposed on an outer surface of a support. At least 20% by weight of the total weight of noble metal particles are adjacent to at least one titanium-containing particle. The noble metal particles have an average diameter of less than 15 nm, and the catalyst has an average diameter of at least 200 microns. A method for preparing methyl methacrylate from methacrolein and methanol using the catalyst is also disclosed.

10 Claims, 3 Drawing Sheets

PROCESS AND CATALYST FOR OXIDATIVE ESTERIFICATION WITH LONG-LIFE CATALYST

BACKGROUND OF THE INVENTION

The invention relates to a catalyst and method for preparing methyl methacrylate from methacrolein and methanol.

Heterogeneous catalysts having noble metals concentrated in an outer region of the catalyst are known, see, e.g., U.S. Pat. No. 6,228,800, for use in producing methyl methacrylate.

WO 2019/057458 discloses a process for preparing a carboxylic ester from an aldehyde via heterogeneous catalysis in a liquid phase in the presence of a catalyst particle. The catalyst particle consists of 0.1% to 3% by weight of gold, 25% to 99.8% by weight of $TiO_2$, 0% to 50% by weight of silicon oxide, 0% to 25% by weight of $Al_2O_3$, 0% to 25% by weight of at least one oxide of an alkali metal, an alkaline earther metal, a rare earth metal, and/or zirconium, 0% to 20% by weight of at least one oxide selected from the group consisting of an iron oxide, a zinc oxide, and a cobalt oxide, and 0% to 5% by weight of at least one other component. The catalyst is preferably composed predominantly or exclusively of gold and $TiO_2$.

However, there is a need for an improved catalyst and process for production of methyl methacrylate that is effective and active for longer lifespans.

SUMMARY OF THE INVENTION

One aspect of the present invention relates to a catalyst comprising noble metal particles and titanium-containing particles, wherein the noble metal particles and titanium-containing particles are disposed on an outer surface of a support, wherein at least 20% by weight of the total weight of noble metal particles are adjacent to at least one titanium-containing particle, wherein the noble metal particles have an average diameter of less than 15 nm and wherein the catalyst has an average diameter of at least 200 microns.

Another aspect of the present invention relates to a method for preparing methyl methacrylate from methacrolein and methanol; said method comprising contacting in a reactor a mixture comprising methacrolein, methanol and oxygen in the presence of a catalyst comprising noble metal particles and titanium-containing particles, wherein the noble metal particles and titanium-containing particles are disposed on an outer surface of a support, wherein at least 20% by weight of the total weight of noble metal particles are adjacent to at least one titanium-containing particle, wherein the noble metal particles have an average diameter of less than 15 nm, and wherein the catalyst has an average diameter of at least 200 microns.

DETAILED DESCRIPTION OF THE INVENTION

Figure 1A:
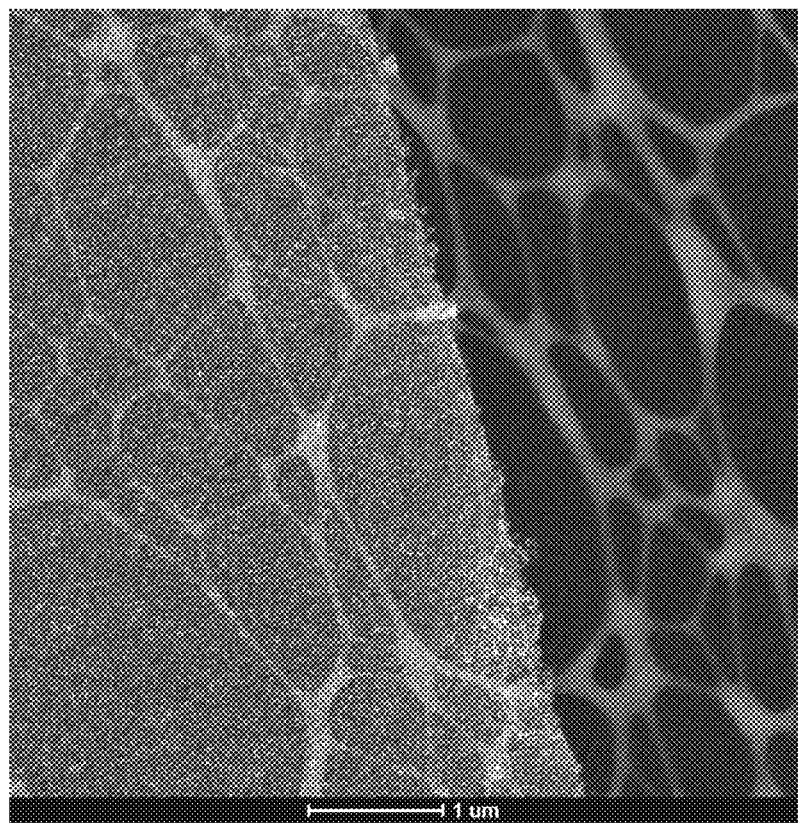
FIGS. 1A and 1B are scanning TEM images of a catalyst according to embodiments of the present invention at different magnification.

All percentage compositions are weight percentages (wt %), and all temperatures are in ° C., unless otherwise indicated. Averages are arithmetic averages unless otherwise indicated. As defined herein, the term "noble metal" is any of gold, platinum, iridium, osmium, silver, palladium, rhodium and ruthenium. More than one noble metal may be present in the catalyst, in which case the limits apply to the total of all noble metals. The "catalyst center" is the centroid of the catalyst particle, i.e., the mean position of all points in all coordinate directions. A diameter is any linear dimension passing through the catalyst center and the average diameter is the arithmetic mean of all possible diameters. The aspect ratio is the ratio of the longest to the shortest diameters. Unless otherwise stated, the average diameter of a particle refers to the average diameter of the particle after the catalyst has been prepared and before the catalyst has been used. An aged catalyst is a catalyst that has been used.

The catalyst of the present invention comprises noble metal particles and titanium-containing particles that are disposed on an outer surface of a support for form a catalyst particle.

The noble metal particles and titanium-containing particles are preferably dispersed on the outer surface of the support. Without wishing to be bound by theory, it is believed that the particles, which are not covalently bound to the surface of the particle, can migrate or move around the surface of the particle. The activity of noble metal particles can vary greatly based on the size of the particles. For example, gold particles become less catalytically active as the size of the particles increases. As the particles migrate, it is possible that the noble metal particles aggregate, which may lead to loss of activity. The present inventors have discovered that dispersing the noble metal particles among titanium-containing particles can surprisingly minimize loss of catalytic activity and provide for longer lasting catalysts.

Preferably, at least 20% by weight of the total weight of noble metal particles are adjacent to titanium-containing particles. In other words, at least 20% by weight of the total weight of noble metal particles are physically contacting a titanium-containing particle. More preferably, at least 30% by weight of the total weight of noble metal particles are adjacent to titanium-containing particles. Even more preferably, at least 40% by weight of the total weight of the noble metal particles are adjacent to titanium-containing particles, and yet more preferably, at least 50% by weight of the total weight of the noble metal particles are adjacent to titanium-containing particles.

The noble metal containing particle have an average diameter of less than 15 nm, preferably less than 12 nm, more preferably less than 10 nm, and even more preferably less than 8 nm.

Preferably, the noble metal is gold or palladium, and more preferably, the noble metal comprises or consists of gold. Preferably, the noble metal comprises at least 75 wt % gold relative to the total amount of the noble metal. More preferably, the noble metal comprises at least 85 wt % gold relative to the total amount of the noble metal.

The titanium-containing particles may comprise elemental titanium or a titanium oxide, $TiO_x$. Preferably, the titanium-containing particles comprise a titanium oxide.

The titanium-containing particles preferably have an average diameter of less than 5 times the average diameter of the noble metal particles, more preferably an average diameter of less than 4 times the average diameter of the noble metal particles, even more preferably an average particle diameter of less than 3 times the average diameter of the noble metal particles, still more preferably an average particle diameter of less than 2 times the average diameter of the noble metal particles, and yet more preferably and average particle diameter of less than 1.5 times the average diameter of the noble metal particles.

The amount by weight of the noble metal particles with respect to the amount of the titanium-containing particles may range from 1:1 to 1:20. Preferably, the weight ratio of noble metal particles to titanium-containing particles ranges from 1:2 to 1:15, more preferably, from 1:3 to 1:10, and even more preferably, from 1:3 to 1:6.

Preferably, the support is a particle of a refractory oxide capable of withstanding long-term use in an oxidative esterification reactor. Materials that are capable of withstanding prolonged use are able to avoid being crushed or pulverized during use. For example, titanium oxide ($TiO_x$) is a support that is highly resistant to acid, but can be mechanically weak when it has a high degree of surface area.

Preferably the support is a particle of γ-, δ-, or θ-alumina, silica, magnesia, zirconia, hafnia, vanadia, niobium oxide, tantalum oxide, ceria, yttria, lanthanum oxide or a combination thereof. Preferably, the support comprises, consists of, or consists essentially of γ-, δ-, or θ-alumina, silica, and magnesia. More preferably, the support comprises, consists of, or consists essentially of silica. As used herein with respect to the support, the phrase "consists essentially of" excludes the presence of materials that would degrade the mechanical strength of the support. Alternatively, "consists essentially of" means that the support comprises at least 95 wt % of the stated material with respect to the total weight of the support.

Preferably, the support has a surface area greater than 10 $m^2/g$, preferably greater than 30 $m^2/g$, preferably greater than 50 $m^2/g$, preferably greater than 100 $m^2/g$, preferably greater than 120 $m^2/g$.

Preferably, the aspect ratio of the catalyst particle is no more than 10:1, preferably no more than 5:1, and preferably no more than 3:1. Although the shape is not limited, preferred shapes for the catalyst particle include spheres, cylinders, rectangular solids, rings, multi-lobed shapes (e.g., cloverleaf cross section), shapes having multiple holes and "wagon wheels;" preferably spheres. Irregular shapes may also be used.

Preferably, at least 90 wt % of the noble metal particles and titanium-containing particles are in the outer 70% of catalyst volume (i.e., the volume of an average catalyst particle), preferably the outer 60% of catalyst volume, preferably the outer 50%, preferably the outer 40%, preferably the outer 35%, preferably in the outer 30%, preferably in the outer 25%. Preferably, the outer volume of any particle shape is calculated for a volume having a constant distance from its inner surface to its outer surface (the surface of the catalyst particle), measured along a line perpendicular to the outer surface. For example, for a spherical particle the outer x % of volume is a spherical shell whose outer surface is the surface of the particle and whose volume is x % of the volume of the entire sphere. Preferably, at least 95 wt % of the noble metal particles and titanium-containing particles are in the outer volume of the catalyst, preferably at least 97 wt %, preferably at least 99 wt %. Preferably, at least 90 wt % (preferably at least 95 wt %, preferably at least 97 wt %, preferably at least 99 wt %) of the noble metal particles and titanium-containing particles are within a distance from the surface that is no more than 30% of the catalyst diameter, preferably no more than 25%, preferably no more than 20%, preferably no more than 15%, preferably no more than 10%, preferably no more than 8%. Distance from the surface is measured along a line which is perpendicular to the surface. Preferably, the noble metal particles and titanium-containing particles form an eggshell structure on the support particles. The eggshell layer may have a thickness of 500 microns or less, preferably 250 microns or less, and more preferably 100 microns or less.

Preferably, the average diameter of the catalyst particle is at least 60 microns, preferably at least 100 microns, preferably at least 200 microns, preferably at least 300 microns, preferably at least 400 microns, preferably at least 500 microns, preferably at least 600 microns, preferably at least 700 microns, preferably at least 800 microns; preferably no more than 30 mm, preferably no more than 20 mm, preferably no more than 10 mm, preferably no more than 5 mm, preferably no more than 4 mm. The average diameter of the support and the average diameter of the final catalyst particle are not significantly different.

Preferably, the amount of noble metal as a percentage of the noble metal and the support is from 0.2 to 5 wt %, preferably at least 0.5 wt %, preferably at least 0.8 wt %, preferably at least 1 wt %, preferably at least 1.2 wt %; preferably no more than 4 wt %, preferably no more than 3 wt %, preferably no more than 2.5 wt %.

According to at least one embodiment, the noble metal particles comprise gold, the titanium-containing particles comprise a titanium oxide, and the support is silica.

Preferably, the catalyst of the present invention maintains a high activity for a long period of time when in use as an oxidative esterification reaction catalyst. Preferably, the catalyst maintains at least 75% of its initial activity after 100 hours of use, more preferably after 500 hours of use, even more preferably after 1000 hours of use, still more preferably after 5000 hours of use, and yet more preferably after 10,000 hours of use. Alternatively, the catalyst maintains at least 75% of its initial activity after 100 hours of simulated use, more preferably after 500 of simulated use, even more preferably after 1000 hours of simulated use, still more preferably after 5000 hours of simulated use, and yet more preferably after 10,000 of simulated use using the simulation method described in the examples below. More preferably, the catalyst maintains at least 80% of its initial activity over 100 hours, 500 hours, 1000 hours, 5000 hours, or 10,000 hours of actual or simulated use. Even more preferably, the catalyst maintains at least 85% of its initial activity over 100 hours, 500 hours, 1000 hours, 5000 hours, or 10,000 hours of actual or simulated use. Still more preferably, the catalyst maintains at least 90% of its initial activity over 100 hours, 500 hours, 1000 hours, 5000 hours, or 10,000 hours of actual or simulated use. Yet more preferably, the catalyst maintains at least 95% of its initial activity over 100 hours, 500 hours, 1000 hours, 5000 hours, or 10,000 hours of actual or simulated use. As used herein, activity is defined as the space time yield (STY) in moles of MMA per hour-kilogram of catalyst as described in the Examples below.

Preferably, the catalyst is produced by precipitating the noble metal and titanium from an aqueous solution of metal salts in the presence of the support. In one preferred embodiment, the catalyst is produced by an incipient wetness technique in which an aqueous solution of a suitable noble metal precursor salt and titanium salt is added to a porous inorganic oxide such that the pores are filled with the solution and the water is then removed by drying. The resulting material is then converted into a finished catalyst by calcination, reduction, or other pre-treatments known to those skilled in the art to decompose the noble metal salts and titanium salts into metals or metal oxides. Preferably, a $C_2$-$C_{18}$ thiol comprising at least one hydroxyl or carboxylic acid substituent is present in the solution. Preferably, the $C_2$-$C_{18}$ thiol comprising at least one hydroxyl or carboxylic acid substituent has from 2 to 12 carbon atoms, preferably 2 to 8, preferably 3 to 6. Preferably, the thiol compound comprises no more than 4 total hydroxyl and carboxylic acid groups, preferably no more than 3, preferably no more than 2. Preferably, the thiol compound has no more than 2 thiol groups, preferably no more than one. If the thiol compound comprises carboxylic acid substituents, they may be present in the acid form, conjugate base form or a mixture thereof. Especially preferred thiol compounds include thiomalic acid, 3-mercaptopropionic acid, thioglycolic acid, 2-mercaptoethanol and 1-thioglycerol, including their conjugate bases.

In one embodiment of the invention, the catalyst is produced by deposition precipitation in which a porous inorganic oxide is immersed in an aqueous solution containing a suitable noble metal precursor salt and a titanium salt and is the salts are then made to interact with the surface of the inorganic oxide by adjusting the pH of the solution. The resulting treated solid is then recovered (e.g. by filtration) and then converted into a finished catalyst by calcination, reduction, or other pre-treatments known to those skilled in the art to decompose the noble metal salts and titanium salts into metals or metal oxides.

Preferably, the process for producing methyl methacrylate (MMA) is performed in an oxidative esterification reactor (OER). The catalyst particles may be present in a slurry or in a catalyst bed, preferably a catalyst bed. The catalyst particles in the catalyst bed typically are held in place by solid walls and by screens or catalyst support grids. In some configurations, the screens or grids are on opposite ends of the catalyst bed and the solid walls are on the side(s), although in some configurations the catalyst bed may be enclosed entirely by screens. Preferred shapes for the catalyst bed include a cylinder, a rectangular solid and a cylindrical shell; preferably a cylinder. The OER further comprises a liquid phase comprising methacrolein, methanol and MMA and a gaseous phase comprising oxygen. The liquid phase may further comprise byproducts, e.g., methacrolein dimethyl acetal (MDA) and methyl isobutyrate (MIB). Preferably, the liquid phase is at a temperature from 40 to 120° C.; preferably at least 50° C., preferably at least 60° C.; preferably no more than 110° C., preferably no more than 100° C. Preferably, the catalyst bed is at a pressure from 0 to 2000 psig (101 kPa to 14 MPa); preferably no more than 2000 kPa, preferably no more than 1500 kPa.

The OER typically produces MMA, along with methacrylic acid and unreacted methanol. Preferably, methanol and methacrolein are fed to the reactor in a methanol:methacrolein molar ratio from 1:10 to 100:1, preferably from 1:2 to 20:1, preferably from 1:1 to 10:1. Preferably, a catalyst bed further comprises inert materials above and/or below the catalyst. Preferred inert materials include, e.g., alumina, clay, glass, silica carbide and quartz. Preferably, the inert material has an average diameter equal to or greater than that of the catalyst, preferably no greater than 20 mm. Preferably, the reaction products are fed to a methanol recovery distillation column which provides an overhead stream rich in methanol and methacrolein; preferably this stream is recycled back to the OER. The bottoms stream from the methanol recovery distillation column comprises MMA, MDA, methacrylic acid, salts and water. In one embodiment of the invention, MDA is hydrolyzed in a medium comprising MMA, MDA, methacrylic acid, salts and water. MDA may be hydrolyzed in the bottoms stream from a methanol recovery distillation column; said stream comprising MMA, MDA, methacrylic acid, salts and water. In another embodiment, MDA is hydrolyzed in an organic phase separated from the methanol recovery bottoms stream. It may be necessary to add water to the organic phase to ensure that there is sufficient water for the MDA hydrolysis; these amounts may be determined easily from the composition of the organic phase. The product of the MDA hydrolysis reactor is phase separated and the organic phase passes through one or more distillation columns to produce MMA product and light and/or heavy byproducts. In another embodiment, hydrolysis could be conducted within the distillation column itself.

One preferred embodiment is a recycle reactor with cooling capacity in the recycle loop. Another preferred embodiment is a series of reactors with cooling and mixing capacity between the reactors.

Preferably, oxygen concentration at a reactor outlet is at least 0.5 mole %, preferably at least 2 mole %, preferably at least 3 mole %; preferably no more than 7 mole %, preferably no more than 6.5 mole %, preferably no more than 6 mole %.

One preferred embodiment of the fixed bed reactor for oxidative esterification is a trickle bed reactor, which contains a fixed bed of catalyst and passes both the gas and liquid feeds through the reactor in the downward direction. In trickle flow, the gas phase is the continuous fluid phase. Thus, the zone at the top of the reactor, above the fixed bed, will be filled with a vapor phase mixture of nitrogen, oxygen, and the volatile liquid components at their respective vapor pressures. Under typical operating temperatures and pressures (50-90° C. and 60-300 psig (400-2000 kPa)), this vapor mixture is inside the flammable envelope if the gas feed is air. Thus, only an ignition source would be required to initiate a deflagration, which could lead to loss of primary containment and harm to the physical infrastructure and personnel in the vicinity. In order to address process safety considerations, a means to operate a trickle bed reactor while avoiding a flammable headspace atmosphere is operation with a gas feed containing a sufficiently low oxygen mole fraction to ensure the oxygen concentration in the vapor headspace is below the limiting oxygen concentration (LOC).

Knowledge of the LOC is required for the fuel mixture, temperature, and pressure of concern. Since the LOC decreases with increasing temperature and pressure, and given that methanol gives a lower LOC than the other two significant fuels (methacrolein and methyl methacrylate), a conservative design chooses a feed oxygen to nitrogen ratio that ensures a composition with less than the LOC at the highest expected operating temperature and pressure. For example, for a reactor operated at up to 100° C. and 275 psig (2 MPa), the feed oxygen concentration in nitrogen should not exceed 7.4 mol %.

EXAMPLES

Example #1

Single Pass Fixed Bed Bubble Column Reactor Operation:

A feed consisting of 20 wt % methacrolein, 200 ppm inhibitor, and a balance of methanol was fed at a rate of 40 g/hr to a ⅜" (9.5 mm) stainless steel tubular reactor containing a short front section of borosilicate glass beads followed by 5 g of catalyst. Catalyst #1 was utilized. A gas containing 8% oxygen in nitrogen was also feed to the reactor at a rate sufficient to obtain 4.5% $O_2$ in the vent. The reactor was operated at 60° C. and 160 psig (400 kPa). The product of the reactor was sent to a liquid-vapor separator and the vapor was sent to a condenser with liquid return and non-condensable gases going to the vent. Results are described in the tables below. Catalyst #1 and Catalyst #8 were run in this manner Catalyst #1 Preparation:

Catalyst #1 was prepared by the incipient wetness technique using 20 g of Fuji Silysia Chemical, Ltd. CARiACT Q-10 silica support as the starting material and adding titanium to the support material. Specifically 10.5 g of titanium isopropoxide along with 3 g of glacial acetic acid were added to the catalyst in rotating equipment to ensure even distribution of the solution to the support material. The solution was at 40° C. when added. The modified support material was then dried under slight vacuum at 60° C. for 4 hrs and then calcined in air at ambient pressure by ramping the temperature at 5° C. per minute from ambient to 125° C., held for 1 hr and then ramped at 5° C. per minute up to 250° C. and held for 1 hr, then ramped at 5° C. per minute to 350° C. and held for 1 hr and finally ramped at 5° C. per minute to 450° C. and held for 4 hrs. Gold was then added to the support by incipient wetness technique utilizing 0.83 g of sodium aurothiosulfate in 10 g of deionized water at 40° C. The resulting catalyst was dried and calcined in air using the same heating profile as above. Analysis with a scanning electron microscope (SEM) equipped with energy-dispersive spectroscopy (EDS) of the catalyst clearly indicates that an eggshell deposition of both Ti and Au exists with the Au preferentially located only where Ti was deposited. The Ti and Au eggshell thickness was found to be approximately 50 microns or less. With an estimated loading of 10 mol % in the outer 50 microns of the 1 mm diameter catalyst, the local loading of titanium is estimated as up to 40 mol % as Ti/(Ti+Si).

Example #2

Batch Recycle Fixed Bed Bubble Column Reactor Operation:

A feed solution of 150 g was prepared comprising 10 wt % methacrolein, 200 ppm inhibitor and a balance of methanol, and placed in a 300 ml Parr® reactor which served as a gas disengagement vessel. The vessel liquid was maintained at a temperature of approximately 20° C. The liquid feed was pumped at 7 mL/min from the gas-disengagement vessel into the bottom of the vertically-oriented fixed bed reactor. Air and nitrogen gas was mixed to obtain 7.8 mol % oxygen and mixed with the liquid feed prior to entering the fixed bed reactor. The fixed bed reactor was a jacketed ¼" (6.4 mm) stainless steel tube maintained at 60° C. using an external heater. The reactor itself was packed with 2 mm glass beads to fill approximately 18 inches (45.7 cm) of the tube, then catalyst. The remaining void at the top of the reactor was filled with 3 mm glass beads. Liquid and gas exiting the top of the reactor were sent to a condenser and non-condensable gases were vented, while the liquid was recycled back into the gas-disengagement vessel. Catalyst #2, as well as the catalysts from examples #3, #4, #5, #7, and #8 below were run in this manner Catalyst #2 Preparation:

Catalyst #2 was prepared by incipient wetness of 4.1 g sodium gold thiosulfate dissolved in 100 g of water to make an aqueous solution and then placed on 100 g of Fuji Silysia Chemical, Ltd. CARiACT Q-20 silica support material. The sample was dried at 120° C. for 1 hr followed by calcination at 400° C. for 4 hr.

Example #3

Catalyst #3 Preparation:

Catalyst #3 was prepared by the following steps. First, a titanium precursor stock solution consisting of 51.7 g of titanium isopropoxide and 28.5 g glacial acetic acid was mixed and stirred at ambient temperature. A support material was then prepared by impregnating 27.9 g of the above mentioned titanium stock solution to the incipient wetness point of 20 g of Fuji Silysia Chemical, Ltd. CARiACT Q-10 silica support material. The sample was then dried at 125° C. for 1 hr, followed by calcination at 250° C. for 1 hr, 350° C. for 1 hr, and 450° C. for overnight with a ramping rate of 5° C. per minute between different temperature settings. Gold deposition was achieved by impregnating a solution containing 0.4 g of sodium gold thiosulfate and 16 g of deionized water to 10 g of the above described support material to its incipient wetness point. The sample was then dried at 120° C. for 1 hr followed by calcination at 400° C. for 4 hr. Analysis with a scanning electron microscope (SEM) equipped with energy-dispersive spectroscopy (EDS) of the catalyst clearly indicates that an eggshell deposition of both Ti and Au exists with the Au preferentially located only where Ti was deposited. The Ti and Au eggshell thickness was found to be approximately 300 microns or less.

Example #4

Catalyst #4 Preparation:

Catalyst #4 was prepared by the following steps. First, a support material was prepared by impregnating titanium isopropoxide to the incipient wetness point of 10 g of Fuji Silysia Chemical, Ltd. CARiACT Q-10 silica support material. The sample was then dried at 125° C. for 1 hr, followed by calcination at 250° C. for 1 hr, 350° C. for 1 hr, 450° C. for 1 hr and 550° C. for 12 hrs with a ramping rate of 5° C. per minute between different temperature settings. Gold deposition was achieved by impregnating a solution containing 0.25 g of sodium gold thiosulfate and 9 g of deionized water to the incipient wetness point of 6 g of the above described support material. The sample was then dried at 120° C. for 1 hr followed by calcination at 400° C. for 4 hrs.

Example #5

Catalyst #5 Preparation:

Catalyst #5 was prepared by the following steps. First, a support material was prepared by impregnating magnesium nitrate hexahydrate to the incipient wetness point of 10 g of Fuji Silysia Chemical, Ltd. CARiACT Q-10 silica support material. The sample was then dried at 120° C. for 1 hr, followed by calcination at 450° C. for 4 hrs with a ramping rate of 5° C. per minute between different temperature settings. A quantity of 8.5 g of titanium isopropoxide and 1.5 g of acetic acid were mixed to provide a titanium precursor solution and 3.1 g of the titanium precursor solution was then impregnated to the above mentioned calcined Mg—$SiO_2$. The sample was then dried at 120° C. for 1 hr, followed by calcination at 550° C. for 6 hrs with a ramping rate of 5° C. per minute between different temperature settings. Gold deposition was achieved by impregnating a solution containing 0.3 g of sodium gold thiosulfate and 8 g of deionized water to the incipient wetness point of 8 g of the above described support material. The sample was then dried at 120° C. for 1 hr followed by calcination at 400° C. for 4 hrs. The resulting sample contained a total of 4.7 wt % Mg and 4 wt % Ti on Si with 1.5 wt % Au loaded on that material. The sample was not assessed to determine if eggshell deposition existed.

TABLE 1

Catalyst Performance

| Catalyst # | Catalyst Description | Catalyst Load (g) | Reactor Type | STY (mol/kg-hr) | Normalized MMA Selectivity (%) |
|---|---|---|---|---|---|
| 1 | Au/Ti—SiO2 | 5 | Single Pass | 4.9 | 98.4 |
| 1 | Au/Ti—SiO2 | 1 | Batch | 4.6 | 98.4 |
| 2 | Au/SiO2 | 2 | Batch | 1.75 | 99.1 |
| 3 | Au/Ti—SiO2 | 1 | Batch | 3.3 | 94.8 |
| 4 | Au/Ti—SiO2 | 1 | Batch | 3.4 | 98.9 |
| 5 | Au/Ti—Mg—SiO2 | 1 | Batch | 5.5 | 98.9 |

\* STY is the space time yield of the catalyst in mol MMA per kg of catalyst – hour. The STY is a measure of catalyst activity. The normalized MMA selectivity is the percent MMA among products originating as methacrolein reactant.

Fresh and Aged Catalyst Comparison

Example #6

Pilot Plant Operation followed by Single Pass Fixed Bed Bubble Column Reactor Operation:

As a first step in the aging process, Catalyst #6 was run in a pilot plant operation for 2000 hours. The reactor was an adiabatic fixed bed reactor operated in and upflow bubble column recycle mode. Air and liquid feed were fed into the bottom of the vertically aligned reactor, a 2-inch (5.1 cm) OD and 1.62-inch (4.1 cm) ID×108 inch (2.7 m) long insulated 316SS tube. The liquid entered the bottom of the reactor through a ⅜" (9.5 mm) line, while the gas was introduced into the bottom via a ⅛" (3.2 mm) line. The product is recycled to provide dilution to the reactor feed and thereby lower the adiabatic temperature rise. The liquid feed is pre-heated to the desired set-point over a series of four jacketed 316SS tubes (⅜" (9.5 mm) OD inner tube with 1" (2.5 cm) OD outer tube). Each of the jacketed sections is 5 feet (1.5 m) long. The reactor product is sent to the gas-liquid separation vessel, which is jacketed and cooled with cooling water. The separation vessel is cooled to minimize unwanted homogeneous chemistry. The temperature inside the vessel varied from 23-28° C. under typical operating conditions over the campaign. The gas-liquid separation tank was agitated at 100 rpm using three impellers. The product leaving the separation tank passes through a 0.1 μm polishing filter before sending to the separations system. The OER product sample is collected after the polishing filter, while the feed sample is collected from the feed mix tank. Typical operating conditions were at or near 50° C. inlet, 280 psig (2 MPA), 40 wt % methacrolein in the feed along with inhibitor and a balance of methanol, and 50% conversion of methacrolein to MMA. A total of 1900 g of catalyst was utilized in the reactor. Air was also feed to the reactor at a rate sufficient to obtain 5% $O_2$ in the vent.

After 2000 hrs of operation in the pilot plant, the catalyst was removed and 5 g of catalyst was placed in a single pass fixed bed bubble column reactor. A feed consisting of 20 wt % methacrolein, 200 ppm inhibitor, and a balance of methanol was fed at a rate of 20 g/hr to a ⅜" (9.5 mm) stainless steel tubular reactor containing a short front section of borosilicate glass beads followed by 5 g of catalyst. A gas containing 8% oxygen in nitrogen was also feed to the reactor at a rate sufficient to obtain 5% $O_2$ in the vent. The reactor was operated at 65° C. and 160 psig (1 MPa). The product of the reactor was sent to a liquid-vapor separator and the vapor was sent to a condenser with liquid return and non-condensable gases going to the vent. The reactor had been operating for over 11 months.

Catalyst #6 Preparation:

The catalyst was Au on 2 mm Cariact Q10 (silica) spheres to which titania had first been added. The catalyst was produced by Clariant. The metal loading was measured by NAA-ICP to be 1.32+/−0.01 wt % Au and 7.1+/−0.1 wt % Ti. Catalyst analysis included transmission electron microscope (TEM), scanning electron microscope (SEM) and energy dispersive x-ray spectrometer (EDS). Fresh catalyst results indicate the average size of the fresh gold nanoparticles was 2.8+/−1.3 nm. Pilot plant and laboratory reactor aged catalyst results indicate the average nanoparticle size grew to 6.0+/−2.3 nm by the end of the 2000 hour pilot plant campaign. Results for Catalyst #6 are shown below in Table 2.

TABLE 2

| Catalyst # | Catalyst Description | Catalyst Load (g) | Reactor Type | STY (mol/kg-hr) | Total Catalyst Operating Time (months) | Normalized MMA Selectivity (%) |
|---|---|---|---|---|---|---|
| 6 | Au/Ti-SiO2 | 1900 | Pilot plant Recycle fixed bed | 4.5 | 0.5 | 96 |
| 6 | Au/Ti-SiO2 | 5 | Single pass | 4.5 | 14 | 98 |

\* STY is the space time yield of the catalyst in mol MMA per kg of catalyst-hour. The STY is a measure of catalyst activity. The normalized MMA selectivity is the percent MMA among products originating as methacrolein reactant.

Example #7

Catalyst #7 Fresh Catalyst Preparation and Scanning TEM Analysis:

A solution was prepared consisting of 0.39 g of sodium gold thiosulfate dissolved in 13.5 g of deionized water and stirred for 30 minutes. This solution was applied to 10 g of Ti-doped CARiACT Q-10 silica which contained 6.6 wt % Ti and had been prepared by Clariant Corporation. The impregnated material was dried for 1 hour at 120° C. and then calcined in a box furnace with a 50 Lph air flow at a temperature of 450° C. (5° C./min ramp) to produce the finished catalyst. The catalyst was analyzed by scanning TEM.

Figure 1B:
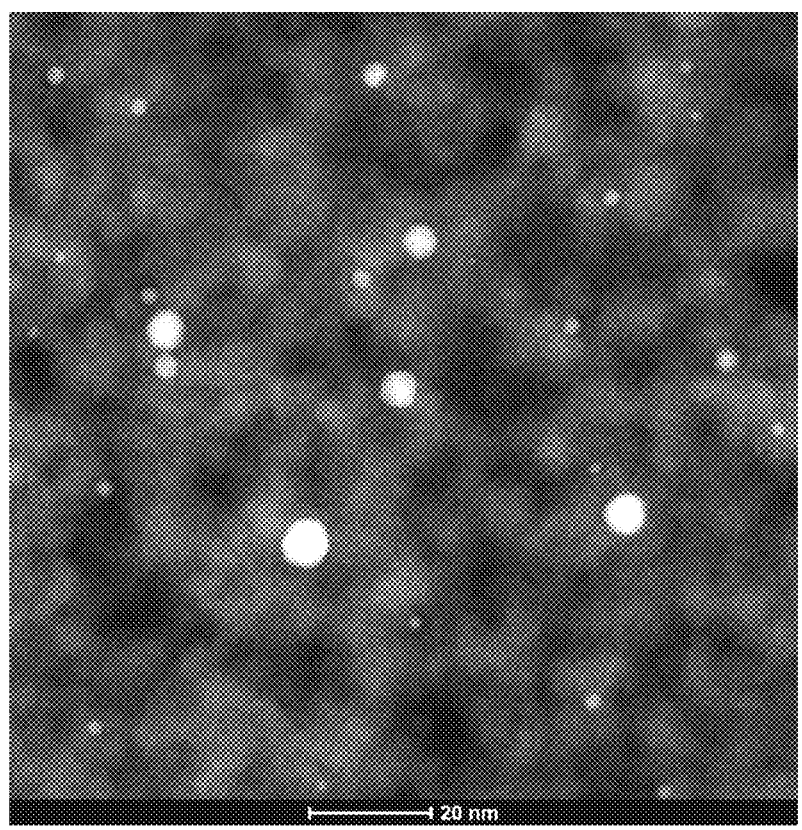

As shown in FIGS. 1A and 1B, TiOx particles of approximately 4.1 nm size were identified on the border of a gold particle. The gold particles, which are seen as bright spots in the scanning TEM image, have an average diameter of less than 10 nm.

Catalyst #7 GAMA Aged Catalyst Preparation and Scanning TEM Analysis:

The fresh catalyst prepared above for the scanning TEM analysis was rapidly aged using a Gold Agglomeration and Movement Assessment (GAMA) aging process to determine whether the catalyst deactivates under conditions similar to a pilot plant aging.

The GAMA testing apparatus consists of a 45 ml Teflon-lined SS Acid Digestion Vessel (rated for a pressure of 1800 psi (12,410 kPa)). 3 g of catalyst were placed in the vessel with 30 ml a methanol solution containing 4 wt % MAA and 6 wt % $H_2O$. The vessel was placed in a box oven at 200° C. for 10 days.

Figure 2A:
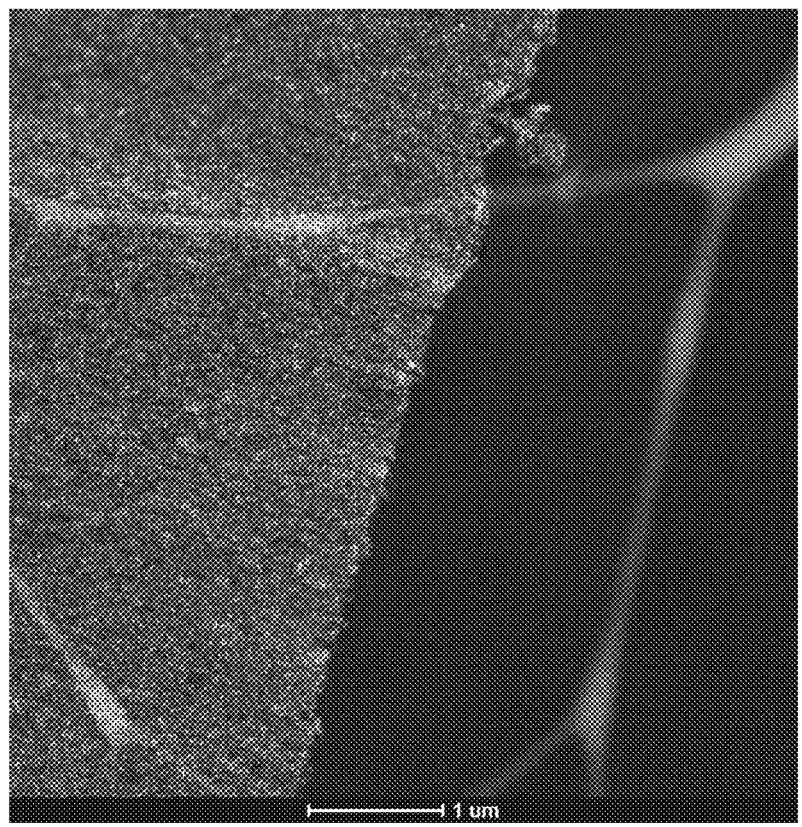
FIGS. 2A, 2B and 2C are scanning TEM images of a catalyst according to embodiments of the present invention at different magnification.
Figure 2B:
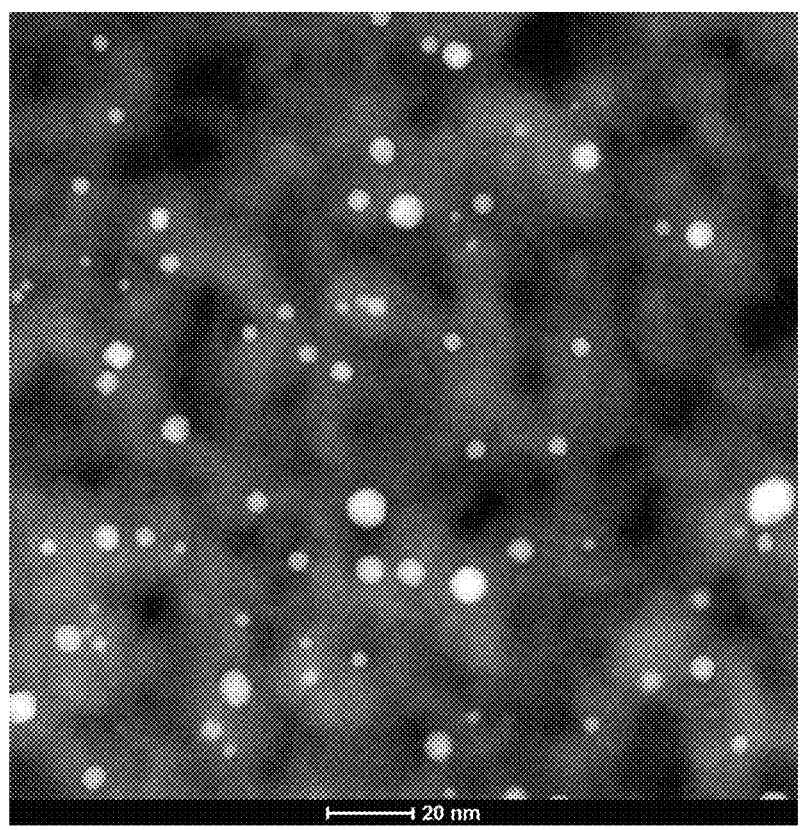
Figure 2C:
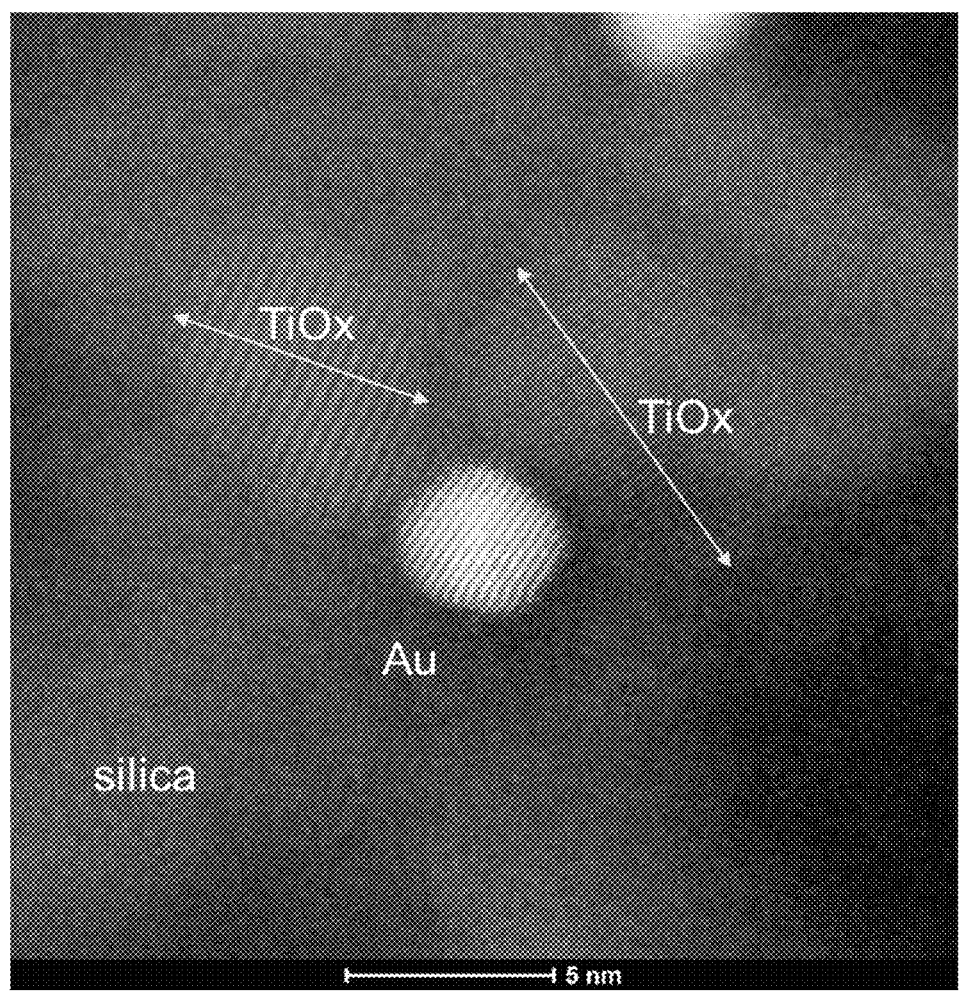

Results of GAMA aging were compared to that of fresh catalyst and are shown below in Table 3. Fresh catalyst had an average gold particle size of 4.1 nm. GAMA aged catalyst had an average gold particle size of 5.1 nm. Scanning TEM images of the GAMA aged catalyst are shown in FIGS. 2A, 2B and 2C.

TABLE 3

| Catalyst # | Catalyst Description | Catalyst Load (g) | Reactor Type | STY (mol/kg-hr) | Catalyst Operating History | Avg. Gold Particle Size (nm) | Normalized MMA Selectivity (%) |
|---|---|---|---|---|---|---|---|
| 7 | Au/Ti-SiO2 | 1 | Batch | 7.5 | Fresh Catalyst | 4.1 | 99.5 |
| 7 | Au/Ti-SiO2 | — | — | — | GAMA Aged Catalyst | 5.1 | — |

* STY is the space time yield of the catalyst in mol MMA per kg of catalyst-hour. The STY is a measure of catalyst activity. The normalized MMA selectivity is the percent MMA among products originating as methacrolein reactant.

Figure 3:
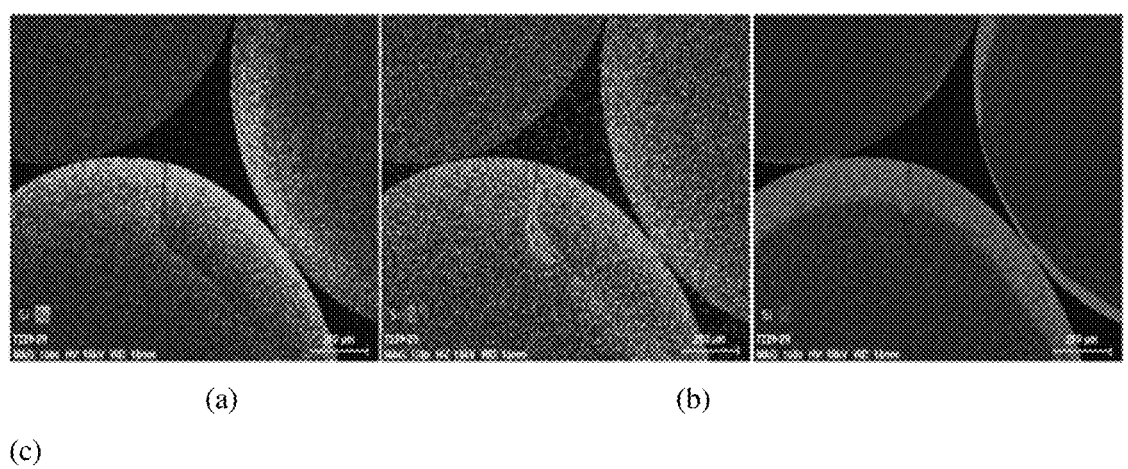
FIG. 3 shows SEM images of a catalyst according to an embodiment of the present invention.

Catalyst #7 SEM Analysis:

The migration of gold nanoparticles was observed using SEM imaging Gold particles formed on the catalyst surface with calcination of the gold sulfur-containing salts (FIG. 3(a)). Once on the surface, the nanoparticles began to migrate (FIG. 3(b)). The gold particles moved away from the sulfur deposits which eventually leached off the catalyst and when the gold particles reached titania particles (FIG. 3(c)), they became anchored to the titania.

Example #8—Comparative Example

The activity of fresh catalyst #8 was measured in the Batch Recycle Fixed Bed Bubble Column Reactor as first described above in Example #2. Following this measurement, the catalyst was GAMA aged. As with catalyst #7, the GAMA testing apparatus consisted of a 45 ml Teflon-lined SS Acid Digestion Vessel into which 3 g of catalyst was placed with 30 ml a methanol solution containing 4 wt % MAA and 6 wt % $H_2O$. The vessel was placed in a box oven at 200° C. for 10 days. Activity of the GAMA aged catalyst was then measured in the Single Pass Fixed Bed Bubble Column Reactor as described above in Example #1. Fresh Catalyst #8 average gold nanoparticle size was estimated by scanning TEM to be 4.0 nm. The GAMA aged catalyst average gold nanoparticle size was estimated by scanning TEM to be 10.3 nm. Results for Catalyst #8 are shown below in Table 4.

Catalyst #8 Preparation:

Catalyst was prepared by incipient wetness of 4.1 g sodium gold thiosulfate dissolved in 100 g of water to make an aqueous solution and then placed on 100 g of Fuji Silysia Chemical, Ltd. CARiACT Q-20C silica support material. The sample was dried at 120° C. for 1 hr followed by calcination at 400° C. for 4 hr.

TABLE 4

| Catalyst # | Catalyst Description | Catalyst Load (g) | Reactor Type | STY (mol/kg-hr) | Catalyst Operating History | Avg. Gold Particle Size (nm) | Normalized MMA Selectivity (%) |
|---|---|---|---|---|---|---|---|
| 8 | Au/SiO2 | 1 | Batch | 2.4 | Fresh Catalyst | 4.0 | 98 |
| 8 | Au/SiO2 | 5 | Single Pass | 1.4 | GAMA Aged Catalyst | 10.3 | 97.7 |

* STY is the space time yield of the catalyst in mol MMA per kg of catalyst-hour. The STY is a measure of catalyst activity. The normalized MMA selectivity is the percent MMA among products originating as methacrolein reactant.

Crush Strength:

The mechanical strength of catalyst or catalyst support particles was directly measured by crushing the particles to the point of mechanical failure. Crush strength testing was carried out using a Mecmesin M100EC. A single particle was placed on the platform and the top plunger was allowed to press on the particle until the load reached a peak value and the material failed. The peak load was recorded using a Shimpo FGE-100× gauge. The test was repeated on 25 individual particles to obtain a statistical average of the crush strength for any given material. Results are shown in Table 5 below.

TABLE 5

Mechanical Strength

| Catalyst # | Material Description | Diameter (mm) | Crush force (kg) | Crush Strength (kg/mm) |
|---|---|---|---|---|
| na | Q-10 | 2.6 | 5.2 | 2.0 |
| 2 | Au/SiO$_2$ | 3.3 | 4.1 | 1.3 |
| 3 | Au/Ti—SiO$_2$ | 3.2 | 6.2 | 1.9 |
| 5 | Au/Ti—Mg—SiO$_2$ | 3.2 | 2.4 | 0.8 |

The invention claimed is:

1. A catalyst comprising noble metal particles and titanium-containing particles, wherein the noble metal particles and titanium-containing particles are disposed on an outer surface of a support, wherein at least 20% by weight of the total weight of noble metal particles are adjacent to at least one titanium-containing particle, wherein the noble metal particles have an average diameter of less than 15 nm, wherein the titanium-containing particles have an average diameter less than 5 times greater than the average diameter of the noble metal particles, and wherein the catalyst has an average diameter of at least 200 microns.

2. The catalyst of claim 1, wherein the noble metal particles comprise at least one noble metal selected from gold and palladium.

3. The catalyst of claim 2, wherein the noble metal particles comprise gold.

4. The catalyst of claim 1, wherein the titanium-containing particles comprise a titanium oxide.

5. The catalyst of claim 1, wherein the support comprises silica.

6. The catalyst of claim 1, wherein at least 25% by weight of the total weight of the noble metal particles are present as single particles or agglomerates of noble metal particles having an average diameter of less than 15 nm.

7. The catalyst of claim 6, wherein at least 40% by weight of the total weight of the noble metal particles are present as single particles of agglomerates of noble metal particles having an average diameter of less than 15 nm.

8. The catalyst of claim 1, wherein at least 40% by weight of the total weight of noble metal particles are adjacent to at least one titanium-containing particle.

9. The catalyst of claim 1, wherein the noble metal particles comprise gold and at least 25% by weight of the total weight of noble-metal particles have an average diameter of less than 15 nm after 1000 hours of use as a catalyst in an oxidative esterification reaction.

10. A method for preparing methyl methacrylate from methacrolein and methanol; said method comprising contacting in a reactor a mixture comprising methacrolein, methanol and oxygen in the presence of a catalyst according to claim 1.

* * * * *